(12) United States Patent
Brouwers et al.

(10) Patent No.: US 9,180,283 B2
(45) Date of Patent: Nov. 10, 2015

(54) SYSTEM FOR TRANSPORTING FLUID ACROSS OR INTO A BIOLOGICAL BARRIER, DEVICE AND CAPSULE AS PART OF THE SYSTEM

(71) Applicant: AMBRO B.V., Den Ham (NL)

(72) Inventors: Arnoldus Maria Brouwers, Den Ham (NL); Bouke Jan Brouwers, Almelo (NL)

(73) Assignee: Ambro B.V., Den Ham (NL)

( * ) Notice: Subject to any disclaimer, the term of this patent is extended or adjusted under 35 U.S.C. 154(b) by 0 days.

(21) Appl. No.: 14/346,425

(22) PCT Filed: Sep. 21, 2012

(86) PCT No.: PCT/NL2012/050669
§ 371 (c)(1),
(2) Date: Mar. 21, 2014

(87) PCT Pub. No.: WO2013/043052
PCT Pub. Date: Mar. 28, 2013

(65) Prior Publication Data
US 2014/0236089 A1    Aug. 21, 2014

(30) Foreign Application Priority Data

Sep. 23, 2011 (NL) .................................. 2007461

(51) Int. Cl.
*A61M 37/00* (2006.01)

(52) U.S. Cl.
CPC ..... *A61M 37/0015* (2013.01); *A61M 2037/003* (2013.01); *A61M 2037/0023* (2013.01)

(58) Field of Classification Search
CPC .................. A61M 2037/0023; A61M 37/0015
USPC .................................................. 604/173, 272
See application file for complete search history.

(56) References Cited

U.S. PATENT DOCUMENTS

| 4,995,751 A * | 2/1991 | Saint Georges Chaumet ....................... 401/135 |
| 2003/0208167 A1* | 11/2003 | Prausnitz et al. ............. 604/272 |

(Continued)

FOREIGN PATENT DOCUMENTS

| WO | WO2007/002521 | 1/2007 |
| WO | WO 2008/101892 A1 | 8/2008 |
| WO | WO2009/077859 | 6/2009 |

OTHER PUBLICATIONS

International search report in application No. PCT/NL2012/050669 with a date of mailing of Dec. 19, 2012.

*Primary Examiner* — Nicholas Lucchesi
*Assistant Examiner* — Gerald Landry, II
(74) *Attorney, Agent, or Firm* — Oppedahl Patent Law Firm LLC

(57) ABSTRACT

The invention relates to a system (1) for transporting fluid across or into a biological barrier, the system comprises a device (10) having a housing with at least one abutment surface for abutting the biological barrier. A capsule is to be received in the housing comprising a substrate (21) from which a plurality of hollow micro needles (22) project and a fluid reservoir (26) which can be brought into fluid communication with the micro needles. According to the invention the capsule comprises a fluid dose and the device comprises a ram (12) arranged movably in the housing for pushing the capsule from a first position to a second position. The ram subsequently proceeds to a third ram position thereby deforming the reservoir for raising the pressure inside the reservoir such that the fluid dose will be transported through the hollow micro needles across or into the biological barrier.

10 Claims, 5 Drawing Sheets

(56) References Cited

U.S. PATENT DOCUMENTS

| | | | |
|---|---|---|---|
| 2005/0096586 A1* | 5/2005 | Trautman et al. | 604/46 |
| 2005/0165358 A1* | 7/2005 | Yeshurun et al. | 604/173 |
| 2006/0142691 A1* | 6/2006 | Trautman et al. | 604/46 |
| 2007/0038181 A1* | 2/2007 | Melamud et al. | 604/158 |
| 2007/0156094 A1* | 7/2007 | Safabash et al. | 604/164.12 |
| 2008/0009802 A1* | 1/2008 | Lambino et al. | 604/173 |
| 2009/0054842 A1 | 2/2009 | Yeshurun | |
| 2010/0305518 A1* | 12/2010 | Moga et al. | 604/272 |
| 2011/0212485 A1 | 9/2011 | Mitragotri | |
| 2011/0251561 A1* | 10/2011 | Inou et al. | 604/173 |
| 2014/0052067 A1* | 2/2014 | Sausse et al. | 604/173 |
| 2014/0296825 A1* | 10/2014 | Lemaire et al. | 604/506 |

* cited by examiner

SYSTEM FOR TRANSPORTING FLUID ACROSS OR INTO A BIOLOGICAL BARRIER, DEVICE AND CAPSULE AS PART OF THE SYSTEM

TECHNICAL FIELD

The invention relates to a system for transporting fluid across or into a biological barrier, which system comprises:

A device that is provided with a housing having at least one abutment surface for abutting the biological barrier;

A substrate from which a plurality of hollow micro needles project, which substrate is to be received in the housing;

A fluid reservoir which can be brought into fluid communication with the micro needles; which reservoir is to be received in the housing;

Wherein the device comprises a displacement mechanism for displacing the substrate and the reservoir relative to the abutment surface from a first position in which the micro needles essentially are present in the housing and a second position from which the micro needles project out of the housing beyond the abutment surface, such that they can penetrate the biological barrier.

BACKGROUND ART

The micro needle approach shows clear advantages over competing methods of transferring fluids through skin or other biological barriers. In contrast to hypodermic needles, micro needles are relatively painless and can be self administered or administered by non-professionals. Furthermore, when using micro needles, only 10-20% of the drug is needed compared to hypodermic needles. In addition, they overcome the molecular size limitations characteristic of conventional transdermal patches.

While hollow micro needles are potentially an effective structure for transferring fluids across or into a biological barrier, the devices proposed to date suffer from a number of drawbacks that limit or prevent their functionality. Current micro needle array devices do not reliably penetrate the biological barrier, preventing or diminishing cross-barrier transfer of fluids. In the case of administering drugs through human skin, the transfer is ineffective if the micro needle does not pierce at least the stratum corneum layer. In many cases, the skin surface is elastic enough to stretch around each micro needle without being pierced.

A system according to the preamble that addresses this drawback is known from US patent application 2005/0165358.

In the known system the displacement mechanism is arranged to achieve a displacement having a non-zero component parallel to a planar surface defined by the substrate. Once the biological barrier is penetrated by the micro needles a user should manually depress a hand-operated cover so as to apply force to a piston which forces the fluid that is present in a storage region through the hollow micro needles to form fine jets there from.

DISCLOSURE OF THE INVENTION

The invention has for its object to provide a system according to the above that only requires one time operation by a user.

The system according to the invention is characterized in that the reservoir and the substrate are incorporated into a capsule comprising a fluid dose, the displacement mechanism comprises a ram arranged movably in the housing from a first to a second ram position in a direction that is substantially perpendicular to the abutment surface for pushing the capsule from the first position to the second position and in that the ram subsequently proceeds to a third ram position thereby deforming the reservoir for raising the pressure inside the reservoir such that the fluid will be transported through the hollow micro needles into the biological barrier substantially all at a time.

In the system according to the invention the ram needs to be activated once by the user and both the penetration of the biological barrier as well as the actual fluid transport across or into the biological barrier is performed in one operation. The ram functions as a two-stage rocket and replaces the displacement mechanism and the piston according to the state of the art mentioned above. The displacement mechanism with ram ensures penetrating the corneum stratum by hollow micro needles at a sufficient rate until a controlled depth is reached as well as raising the pressure in the capsule for pressing the fluid through the hollow micro needles In addition the system according to the invention provides a compact design with an elegant and simple operation. The system according to the invention is patient friendly and allows for self-injection. It is thus suitable for daily use by any individual. It is also suitable for use in large groups, particularly in case of vaccination and even in case of urgent calamities, for instance due to an outbreak of a lethal virus, such as sars, ebola etcetera.

US 2006/0142691 describes an apparatus for piercing skin with a micro protrusion member formed by a patch comprising an array of coated micro needles.

It is noted that the known apparatus comprises a housing having at least one abutment surface for abutting the biological barrier, wherein the device comprises a displacement mechanism for displacing the patch substrate relative to the abutment surface from a first position, in which the micro needles essentially are present in the housing, to a second position from which the micro needles project out of the housing beyond the abutment surface, such that they can penetrate the biological barrier, wherein the displacement mechanism comprises a ram arranged movably in the housing from a first to a second position in a direction that is substantially perpendicular to the abutment surface for pushing the patch substrate from the first position to the second position.

The known apparatus is not suitable for transporting fluid across or into a biological barrier by means of hollow micro needles as the fluid will be pressed out of the needles before they can sufficiently pierce the skin.

According to a first preferred embodiment the displacement mechanism further comprises pre-tensioning means for pre-tensioning the ram in an initial position and an eccentrical drive for releasing the pre-tensioning means. Suitable pre-tensioning means, such as one or more springs, render the micro needles with a high enough velocity to penetrate all types of biological barriers, more specifically to penetrate even the relatively hard outer skin layers of human beings. Use of an eccentrical drive for releasing the pre-tensioning means allows for a controlled acceleration of the ram, wherein the eccentrical drive functions as a shock absorber thus enhancing user comfort.

According to a further preferred embodiment the housing comprises a stop member and the reservoir or the substrate comprises at least one shoulder, which shoulder rests against the stop member in the second position. By using a stop member and at least one cooperating shoulder the second position of the reservoir and the substrate is precisely defined.

According to yet a further embodiment the material of the reservoir is deformable allowing raising the pressure inside the reservoir by movement of the ram pushing against the reservoir. In an elegant embodiment the reservoir is generally dome shaped and the dome comprises a contact area for the ram.

Optimal hygiene for users is assured in a further embodiment in which the capsule is intended for one time use only. Optionally a skin stretching ring also forms part of the capsule, wherein the reservoir and the substrate are mounted for displacement relative to the skin stretching ring.

The invention further relates to a device described as part of the system according to the invention.

The invention also relates to a capsule described as part of the system according to the invention.

BRIEF DESCRIPTION OF THE DRAWINGS

The invention will now be elucidated in more detail herein below with reference to the drawings, in which.

BEST MODE TO CARRY OUT THE INVENTION

Figure 1:
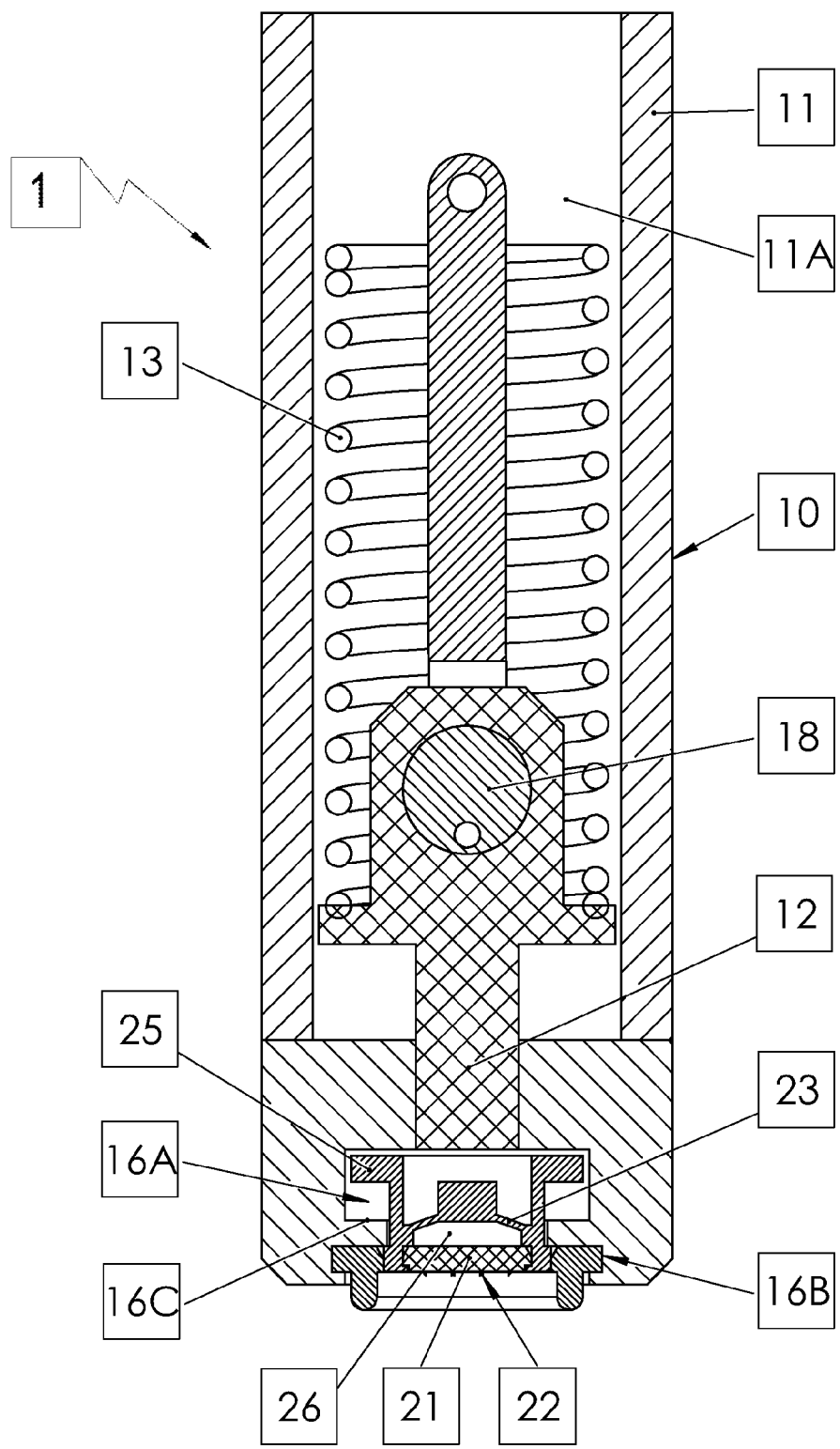
FIG. 1 shows a cross sectional view of a preferred embodiment of the system according to the invention in a first position.

FIG. 1 shows a cross sectional view on a preferred embodiment of the system according to the invention. System 1 comprises a device 10 having a housing 11 in which a capsule 20 can be inserted.

Figure 2A:
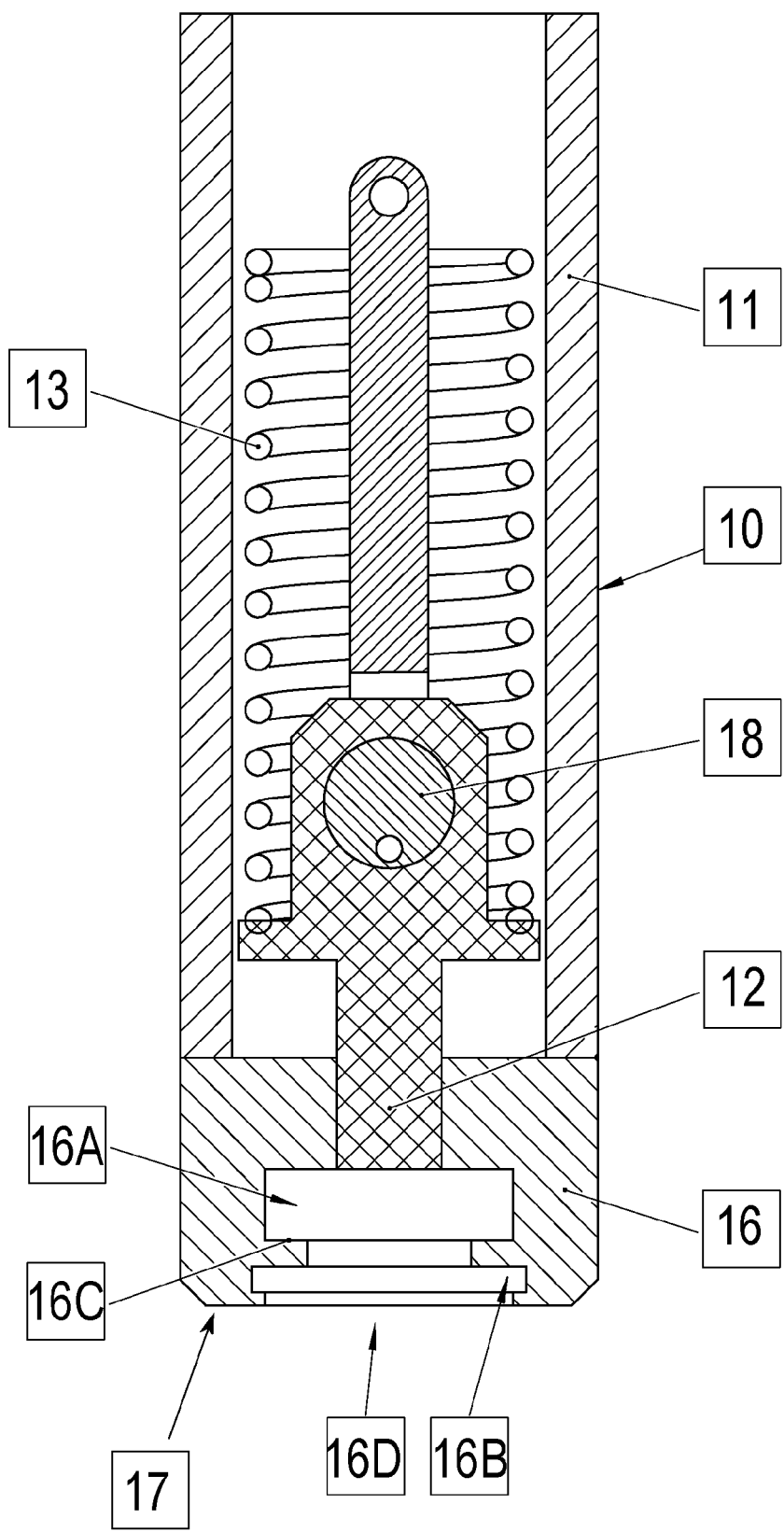
FIG. 2A shows a cross sectional view of a device as part of the system in FIG. 1.

FIG. 2A shows a cross sectional view of device 10. Device 10 can also be described as an applicator for transporting fluid present in the capsule 20 across or into a biological barrier. One surface of the end part 16 is intended as an abutment surface 17 for abutting the biological barrier, for instance human skin. In the preferred embodiment a skin stretching ring 30 is used for stretching the skin before transporting the fluid. Such a stretching ring is optional and in the preferred embodiment actually forms the abutment surface.

The housing 11 is preferably hand held housing. The housing 11 is elongate and has a hollow inner space.

Figure 3A:
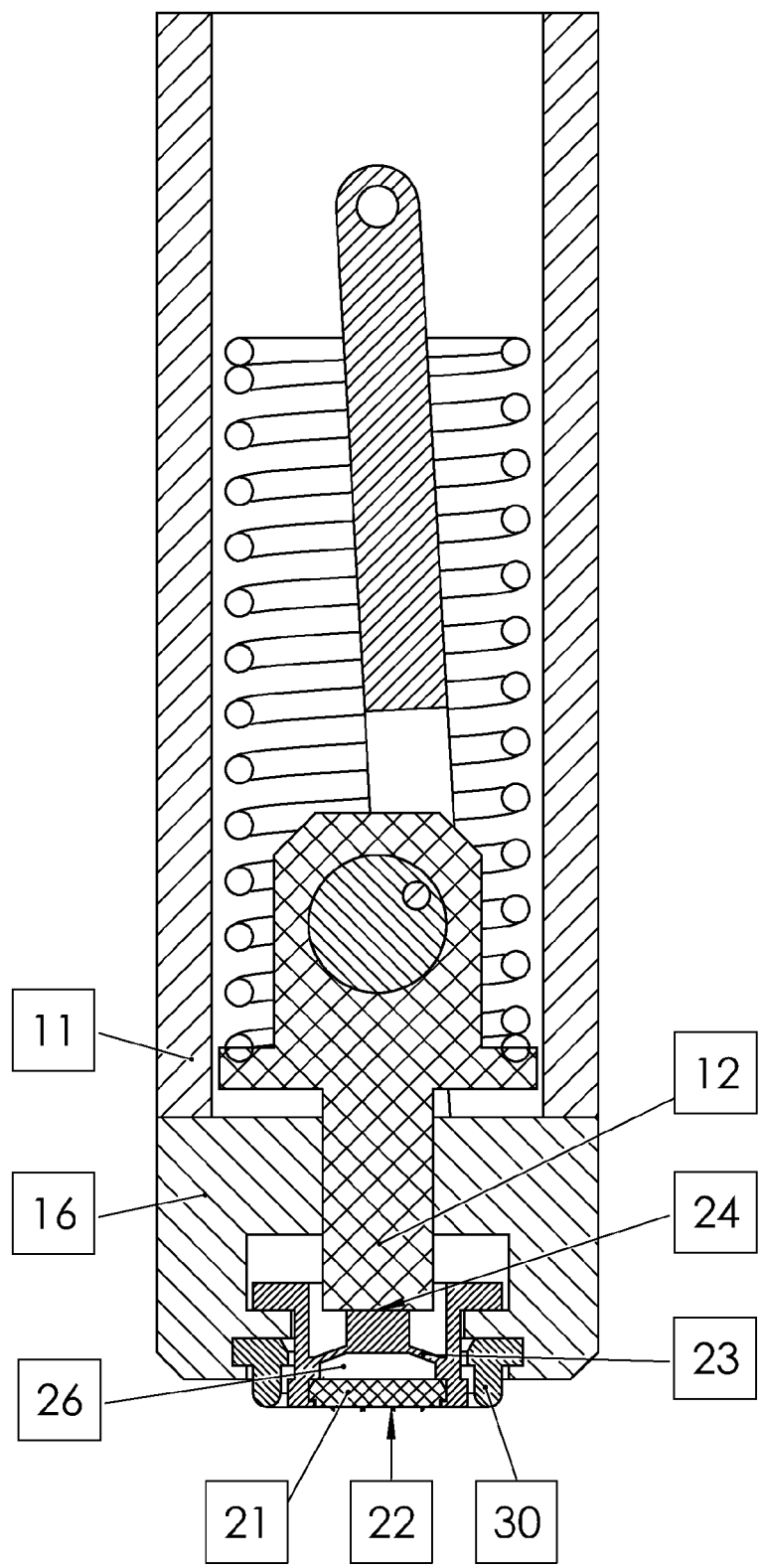
FIG. 3A shows a cross sectional view of the system in FIG. 1 in a second position.
Figure 3B:
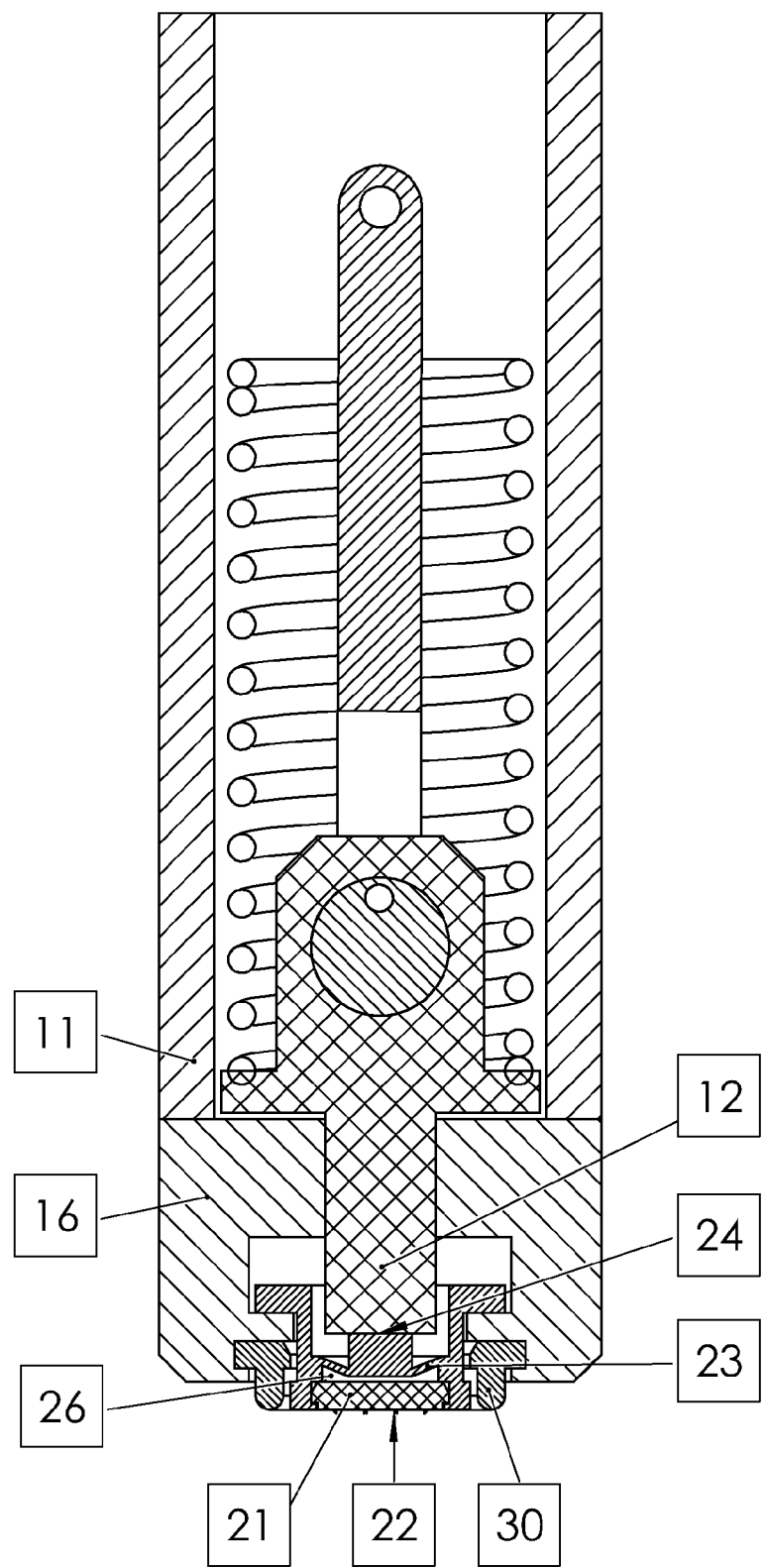
FIG. 3B shows a cross sectional view of the system in FIG. 1 in a third position.

In the housing a displacement mechanism is present that is arranged to push capsule 20 into different positions, which are shown in FIGS. 3A and 3B.

Figure 2B:
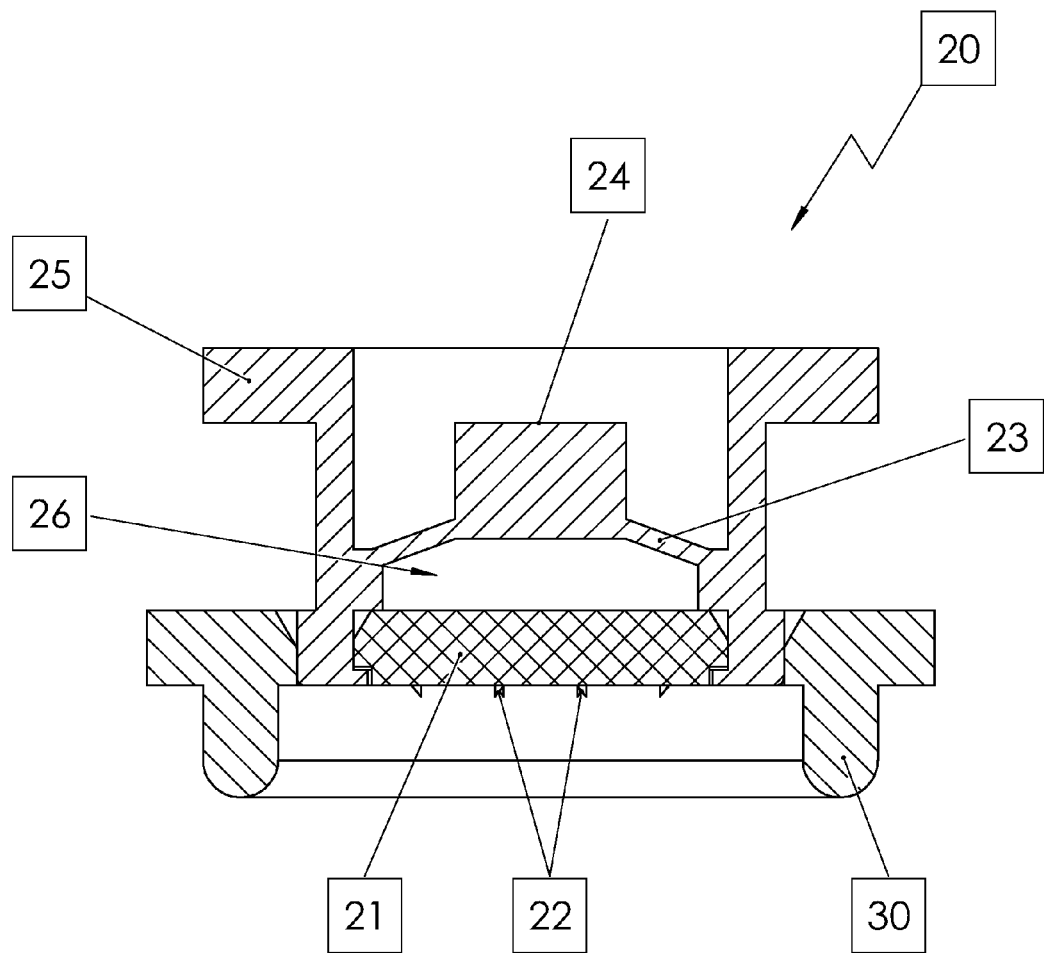
FIG. 2B shows a cross sectional view of a capsule as part of the system in FIG. 1.

FIG. 2B shows a cross sectional view of the capsule 20. The fluid to be transported is contained in a fluid reservoir 26. This fluid reservoir 26 is or can be brought into fluid communication with a plurality of hollow micro needles 22 that project from a substrate 21. In the preferred embodiment shown the capsule 20 comprises both the substrate 21 with hollow micro needles as well as the fluid reservoir 26. The displacement mechanism is arranged to displace the substrate and the reservoir relative to the abutment surface or stretching ring 30. The displacement involves displacement between a first initial position that is shown in FIG. 1 to a second position shown in FIG. 3A. End part 16 is provided with an opening through which capsule 20 can be inserted.

The capsule 20 comprises at least one shoulder 25 that in the first position lies against the distal surface of the first space 16A. In the second position the shoulder lies against the stop member 16C present on the proximal end surface of the first space 16A. In the first position the micro needles 22 do not project beyond the abutment surface, which in this case is formed by ring 30. In the second position the micro needles 22 do project out of the housing 11 beyond the abutment surface, such that they will be able to penetrate the biological barrier.

The displacement mechanism is further arranged to displace the fluid from the reservoir 26 through the hollow micro needles 22 across or into the biological barrier. In the preferred embodiment the displacement mechanism is arranged to raise the pressure inside the reservoir 26 such that the fluid will be transported through the hollow micro needles 22 into the biological barrier. Thereto the displacement mechanism proceeds to a third position, shown in FIG. 3B in which the displacement mechanism deforms the reservoir 26. To this end the material of the reservoir is deformable. In the preferred embodiment the reservoir 26 is generally dome shaped and the dome 23 comprises a contact area 24 for a ram 12 forming part of the preferred displacement mechanism.

The displacement mechanism further comprises pre-tensioning means for pre-tensioning the ram 12 in a starting position. This starting position is shown in FIG. 1. In the preferred embodiment shown the pre-tensioning means comprise a drive 18 for eccentrically driving the ram 12. In the first initial position of the displacement mechanism the eccentrical drive 18 is placed in an off centre position. When the system is activated by the user drive 18 turns at least partly around thereby facilitating a controlled acceleration of the ram 12 by the pre-tensioning means towards the second position and finally into the third position.

Preferably the pre-tensioning means comprise a spring 13. The necessary force to be delivered by the spring depends on the application. When the target area to be reached by the micro needles lies in the epidermis of human skin a force of 15-25 kg, more preferably 20 kg is expected to be sufficient.

It is noted that other suitable pre-tensioning means include electrical pre-tensioning means, for instance arranged to charge a capacitor, or pneumatical pre-tensioning means for instance arranged to pressurise an air vessel.

The ram 12 is arranged movably in the hollow space 11A of the housing 11 in a direction that is substantially perpendicular to the abutment surface 17, 30 towards an opening 16D in the abutment surface of the end part.

In the preferred embodiment shown the ram 12 is displaced mechanically by eccentrically driven pre-tensioning means (13, 18). Alternatively the ram can be displaced by a linear actuator or a pneumatic actuator.

In the preferred embodiment shown the housing has an end part 16 that comprises a first space 16A and a second space 16B which are in connection with the opening 16D in the abutment surface. The first space 16A is arranged to receive the shoulder 25 of the capsule 20. The second space 16B is arranged to receive the tensioning ring 30. The first space 16A comprises a stop member 16C for shoulder 25 to stop movement of the capsule 20 when it has reached the second position.

In the preferred embodiment shown the stretching ring 30 is received in the second space 16B together with the substrate 21. The substrate 21 is displaceable relative to the stretching ring 30.

Typically, the reservoir 26 is attached to, or integrated into, the substrate 21, either integrally (as in a one-piece device) or at the moment of fluid delivery (as with a Luer-lock type device). In the preferred embodiment the reservoir 26 and the substrate 21 are incorporated into a capsule 20 that is intended for one time use only.

Optionally the stretching ring 30 can form part of the capsule 20 as well. In this embodiment the rest of the capsule is mounted for displacement relative to the stretching ring.

After use of the system, the capsule may be discarded and the pre-tensioning means can be reset to the initial position, in which the device 10 is ready for re-use. The resetting can be performed manually or automatically.

The system according to the invention is suitable for use with humans as well as animals. Examples of biological barriers include: skin, vessel walls, intestinal walls, the eye et cetera.

The micro needles 22 are hollow; that is, each contains at least one substantially annular bore or channel having a diameter large enough to permit passage of a drug-containing fluid through the micro needle. The hollow shafts may be linear, i.e. extend upwardly from needle base to needle tip, or they may take a more complex path, e.g. extend upwardly from the needle base, but then lead to one or more 'portholes' or 'slits' on the sides of the needles, rather than an opening at the needle tip.

The micro needles can be constructed from a variety of materials, including metals, ceramics, semiconductors, organics, polymers, and composites. Preferred materials of construction include pharmaceutical grade stainless steel, gold, titanium, nickel, iron, tin, chromium, copper, palladium, platinum, alloys of these or other metals, silicon, silicon dioxide, and polymers.

The length of the micro needles is selected for the particular application, accounting for both an inserted and uninserted portion. An array of micro needles can include a mixture of micro needles having, for example, various lengths, outer diameters, inner diameters, cross-sectional shapes, and spacings between the micro needles. In transdermal applications, the "insertion depth" of the micro needles is preferably less than about 100-150 µm, so that insertion of the micro needles into the skin does not penetrate into the dermis, thereby avoiding contacting nerves which may cause pain. In such applications, the actual length of the micro needles typically is longer, since the portion of the micro needles distal the tip lies in the substrate and cannot be inserted into the skin; the uninserted length depends on the particular device design and configuration. The actual (overall) height or length of micro needles should be equal to the insertion depth plus the uninserted length and may be about two millimeters. The length of the part of the micro needles extending from the substrate typically lies between about 10 µm and 2 mm, preferably between 100 µm and 500 µm, and more preferably between 150 µm and 350 µm for transdermal applications and between 500 and 800 µm for subcutaneous applications.

Essentially any fluid can be delivered using the micro needle devices described herein. Typically the fluid comprises an agent which possesses therapeutic, prophylactic, or diagnostic properties in vivo, for example when administered to a human or an animal. Examples of suitable therapeutic and/or prophylactic active agents include proteins, such as hormones, antigens, such as vaccines, and growth factors; nucleic acids, such as antisense molecules; and smaller molecules, such as antibiotics, steroids, decongestants, neuroactive agents, anaesthetics, and sedatives. Examples of suitable diagnostic agents include radioactive isotopes and radio opaque agents, metals, gases, labels including chromatographic, fluorescent or enzymatic labels.

In a preferred embodiment, the reservoir is formed of a deformable material. Examples of suitable deformable materials include metals or metal foils or elastic materials, such as elastomeric polymer or rubber.

The reservoir is selectably in fluid communication with the micro needle bore, such that the reservoir contents can flow from the reservoir and out through the micro needle tip, into the target tissue. Typically, it is attached to, or integrated into, the substrate, either integrally (as in a one-piece device) or at the moment of fluid delivery (as with a Luer-lock type device). The reservoir is to provide suitable, leak-free storage of the agent composition before it is to be delivered. Together the substrate and the reservoir form a capsule. In the context of the present invention a capsule is meant to be an enclosure filled with a fluid dose, i.e. a predetermined amount of fluid to be transported substantially all at a time.

The skin stretching ring is suitable for tensioning human skin to facilitate penetration of the stratum corneum. The ring also serves as a protective member for the hollow micro needles. Any suitable skin friendly material, preferably plastic or stainless steel may be used for the skin stretching ring.

The invention is of course not limited to the described and shown preferred embodiment. The invention relates generally to any embodiment falling within the scope of protection as defined in the claims and as seen in the light of the foregoing description and accompanying drawings.

The invention claimed is:

1. A system for transporting fluid across or into a biological barrier, which system comprises:
    a device that is provided with a housing having at least one abutment surface for abutting the biological barrier;
    a substrate from which a plurality of hollow micro needles project, which substrate is to be received in the housing;
    a fluid reservoir which can be brought into fluid communication with the micro needles;
    which reservoir is to be received in the housing;
    wherein the device comprises a displacement mechanism that comprises a ram arranged movably in the housing from a first to a second ram position in a direction that is substantially perpendicular to the abutment surface for displacing the substrate and the reservoir relative to the abutment surface from a first position, in which the micro needles essentially are present in the housing, to a second position from which the micro needles project out of the housing beyond the abutment surface, such that they can penetrate the biological barrier, wherein the reservoir and the substrate are incorporated into a capsule to be inserted in the housing, said capsule being an enclosure comprising a fluid dose,-the housing comprises an end part for receiving the capsule, the abutment surface being provided on the end part, the ram is arranged to displace the capsule by pushing the capsule from the first position to the second position in the end part, and in that the ram subsequently proceeds to a third ram position thereby deforming the reservoir for raising the pressure inside the reservoir such that the fluid dose will be transported through the hollow micro needles across or into the biological barrier substantially all at a time.

2. A system according to claim 1, wherein the displacement mechanism further comprises pre-tensioning means for pre-tensioning the ram in an initial position.

3. A system according to claim 2, wherein the displacement mechanism further comprises an eccentrical drive for releasing the pre-tensioning means.

4. A system according to claim 1, wherein the housing comprises a stop member and wherein the reservoir or the substrate comprises at least one shoulder, which shoulder rests against the stop member in the second position.

5. A system according to claim 1, wherein the material of the reservoir is deformable.

6. A system according to claim 5, wherein the reservoir is generally dome shaped and the dome comprises a contact area for the ram.

7. A system according to claim 1, wherein the capsule is intended for one time use only.

8. A system according to claim 7, wherein a skin stretching ring also forms part of the capsule, wherein the reservoir and the substrate are mounted for displacement relative to the skin stretching ring.

9. A device for transporting fluid across or into a biological barrier that is provided with a housing having at least one abutment surface for abutting the biological barrier, wherein the device comprises a displacement mechanism that comprises a ram arranged movably in the housing from a first to a second ram position in a direction that is substantially perpendicular to the abutment surface, characterised in that the housing comprises an end part for receiving a capsule to be inserted in the housing, said capsule being an enclosure comprising a fluid dose, the abutment surface being provided on the end part, the ram is arranged to displace the capsule by pushing the capsule from the first position to the second position in the end part, and in that the ram subsequently proceeds to a third ram position thereby deforming the capsule for raising the pressure inside the reservoir such that the fluid dose will be transported across or into the biological barrier substantially all at a time.

10. A capsule-comprising a substrate from which a plurality of hollow micro needles project and a fluid reservoir which can be brought into fluid communication with the micro needles, said capsule being an enclosure comprising a fluid dose.

\* \* \* \* \*